US010858310B1

(12) United States Patent
Cozzula et al.

(10) Patent No.: US 10,858,310 B1
(45) Date of Patent: Dec. 8, 2020

(54) METHOD FOR PRODUCING ISOCYANATES

(71) Applicant: Covestro Deutschland AG, Leverkusen (DE)

(72) Inventors: Daniela Cozzula, Sankt Katharinen (DE); Andreas Ernst, Aachen (DE); Matthias Leven, Cologne (DE); Walter Leitner, Aachen (DE); Thomas Ernst Mueller, Aachen (DE); Christoph Guertler, Cologne (DE); Stefan Wershofen, Mönchengladbach (DE); Gernot Jaeger, Cologne (DE); Franz Beggel, Cologne (DE); Jens Langanke, Mechernich (DE)

(73) Assignee: Coverstro Deutschland AG, Leverkusen (DE)

( * ) Notice: Subject to any disclaimer, the term of this patent is extended or adjusted under 35 U.S.C. 154(b) by 0 days.

(21) Appl. No.: 16/639,899

(22) PCT Filed: Aug. 31, 2018

(86) PCT No.: PCT/EP2018/073512
§ 371 (c)(1),
(2) Date: Feb. 18, 2020

(87) PCT Pub. No.: WO2019/043180
PCT Pub. Date: Mar. 7, 2019

(30) Foreign Application Priority Data

Sep. 4, 2017 (EP) ..................... 17189248

(51) Int. Cl.
C07C 263/04 (2006.01)
B01J 31/02 (2006.01)
B01J 27/055 (2006.01)

(52) U.S. Cl.
CPC ........... C07C 263/04 (2013.01); B01J 27/055 (2013.01); B01J 31/0208 (2013.01); B01J 31/0225 (2013.01); B01J 31/0238 (2013.01); B01J 2231/64 (2013.01); B01J 2531/002 (2013.01)

(58) Field of Classification Search
CPC ... C07C 263/04; B01J 31/0225; B01J 27/055; B01J 31/0238; B01J 31/0208; B01J 2531/002; B01J 2231/64; B01J 31/0202
See application file for complete search history.

(56) References Cited

U.S. PATENT DOCUMENTS 3,404,170 A * 10/1968 Ulrich ................... C07C 265/14
560/345
3,919,279 A * 11/1975 Rosenthal ............. C07C 265/14
560/345
4,081,472 A * 3/1978 Tsumura ............... C07C 263/04
560/345
4,486,449 A 12/1984 Kisida et al.
5,502,244 A * 3/1996 Okawa ................... C07C 263/04
560/345
8,871,965 B2 10/2014 Franzke et al.
2010/0113823 A1 * 5/2010 Shinohata ............. C07C 263/04
560/344
2016/0145201 A1 5/2016 Kojima et al.

FOREIGN PATENT DOCUMENTS

CN 101337189 A 1/2009
EP 0672653 A1 9/1995
JP 2011162442 A 8/2011
KR 970004412 3/1997

OTHER PUBLICATIONS

Uriz, P. et al, Tetrahedron Letters (43), 2002, 1673-1676, "A new and efficient catalytic method for synthesizing isocyanates from carbamates".
Gastaldi, S. et al, J. Org. Chem. (63), 2000, 3239-3240, "Diidosilane: A Reagent for Mild, Efficient Conversion of Carbmates to Ureas via Isocyanates".
Wang, J. et al., Applied Catalysis A: General, 2004, 261, 191-197), "A new non-phosgene route for synthesis of methyl N-phenyl carbamate from phenylurea and methanol".
Gasperini, M. et al., Adv. Syn. Cat., 2005, 347, 105-120), "Carbonylation of Dinitrotoluene to Dimethyl Toluenedicarbamate; High Efficiency of Phosphorus Acids as Promoters for the Palladium-Phenanthroline Catalytic System".
Fukuoka, Shinsuke et al, J. Chem. Soc., Chem. Commun., 1984, p. 399.
Mizuno, Takumi et al, Tetrahedron 50 (1994) 5669-5680, "Novel Synthesis of S-Alkyl Thiocarbamates from Amines, Carbon Monoxide, Elemental Sulfur, and Allkyl Halides in the Presence of a Selenium Catalyst".
Mizuno, Takumi et al, Tetrahedron 59 (2003) 1327-1331, "Facile S-alkyl thiocarbamate synthesis by a novel DBU-assisted carbonylation of amines with carbon monoxide and sulfur".

(Continued)

Primary Examiner — Robert C Boyle
(74) Attorney, Agent, or Firm — Donald R. Palladino

(57) ABSTRACT

The invention relates to a method for producing an isocyanate, wherein a carbamate or thiolcarbomate is converted, in the presence of a catalyst, with separation of an alcohol or thioalcohol, at a temperature of at least 150° C., to the corresponding isocyanate, wherein a compound of the general formula (X)(Y)(Z—H) is used as a catalyst, in particular characterized in that the compound has both a proton donor function and a proton acceptor function. In the catalysts according to the invention, a separable proton is bound to a heteroatom, which is more electronegative than carbon. Said heteroatom is either identical to Z or a component thereof. In the catalysts according to the invention, there is additionally a proton acceptor function which is either identical to X or a component thereof. According to the invention, the proton donator and proton acceptor function are connected to each other by the bridge Y.

15 Claims, No Drawings

(56) References Cited

OTHER PUBLICATIONS

Mizuno, Takumi et al, Tetrahedron 60 (2004) 2869-2873, "Practical synthesis of S-alkyl thiocarbamate herbicides by carbonylation of amines with carbon monoxide and sulfur".
Grzyb, Justyna A. et al, Tetrahedron 61 (2005) 7153-7175, "Carbamoylimidazolium and thiocarbamoylimidazolium salts: novel reagents for the synthesis of ureas, thioureas, carbamates, thiocarbamates and amides".
Wynne, James H. et al, J. Org. Chem. 68 (2003) 3733-3735, "Facile One-Pot Synthesis of S-Alkyl Thiocarbamates".
Nishiyama, Yutaka et al, J. Org. Chem. 70 (2005) 2551-2554, "A Facile Method for the Synthesis of Thiocarbamates: Palladium-Catalyzed Reaction of Disulfide, Amine, and Carbon Monoxide".
International Search Report, PCT/EP2018/073512, dated Nov. 22, 2018, Authorized officer: Irmgard Seitner.

* cited by examiner

METHOD FOR PRODUCING ISOCYANATES

CROSS-REFERENCE TO RELATED APPLICATION

This application is a national stage application under 35 U.S.C. § 371 of PCT/EP2018/073512, filed Aug. 31, 2018, which claims the benefit of European Application No. 17189248.2, filed Sep. 4, 2017, both of which are incorporated by reference herein.

FIELD

The invention relates to a process for producing an isocyanate in which a carbamate or thiolcarbamate is converted into the corresponding isocyanate in the presence of a catalyst with elimination of an alcohol or thioalcohol at a temperature of at least 150° C., wherein the catalyst used is a compound of general formula (X)(Y)(Z—H) which is especially characterized in that it has both a proton donor function and a proton acceptor function. In the catalysts according to the invention, an abstractable proton is bonded to a heteroatom that is more electronegative than carbon. This heteroatom is either identical to Z or is a constituent thereof. A proton acceptor function which is either identical to X or is a constituent thereof is further present in the catalysts according to the invention. The proton donor function and proton acceptor function are joined to one another via the bridge Y.

BACKGROUND

Isocyanates are produced in large volumes and serve mainly as starting materials for the production of polyurethanes. They are usually produced by reacting the corresponding amines with phosgene. The reaction of the amines with the phosgene can be effected either in the gas phase or in the liquid phase, wherein the reaction may be conducted discontinuously or continuously. There is global use both of aromatic isocyanates, for example methylene diphenyl diisocyanate (MMDI—"monomeric MDI"), polymethylene polyphenylene polyisocyanate (a mixture of MMDI and higher homologs, PMDI, "polymeric MDI") or tolylene diisocyanate (TDI), and of aliphatic isocyanates, for example pentane diisocyanate (PDI), hexamethylene diisocyanate (HDI) or isophorone diisocyanate (IPDI).

One alternative to the reaction of primary amines with phosgene is carbamate cleavage:

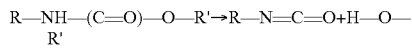

R and R' denote organic radicals. It is also possible to convert thio/carbamates R—NH—(C═O)—S—R' into isocyanates with elimination of a thioalcohol H—S—R'.

The carbamate cleavage can be effected thermally or be mediated by catalysts or stoichiometrically employed auxiliary reagents. The thermal cleavage generally takes place above a temperature of approx. 180° C. As catalysts or auxiliary reagents for the catalytic carbamate cleavage, a very wide variety of classes of compounds have been described. Some examples are mentioned below:

A publication in Tetrahedron Letters (43), 2002, 1673-1676 (P. Uriz et al.) is concerned with the use of the phyllosilicate montmorillonite K10 as a catalyst for the carbamate cleavage. It is hypothesized here that the carbamates are protonated via the Brønsted acid centers present and are cleaved by subsequent transprotonation to give the isocyanate and alcohol.

CN 000101337189 also describes the use of solid acids of the type SO42-/TiO₂—ZnO—ZrO₂—Al₂O₃ prepared from titanates (8 to 45 mol %), water-soluble zinc salts (30 to 60 mol %), water-soluble aluminum salts (3 to 10 mol %), water-soluble zirconium salts (8 to 20 mol %) and also sulfuric acid (6 to 18 mol %).

A publication in J. Org. Chem. (63), 2000, 3239-3240 (S. Gastaldi et al.) describes the use of diisopropylethylamine ("Hünig's base") and SiI₂H₂ in the carbamate cleavage. Both are used stoichiometrically in this case.

Patent application EP 0 672 653 A1 describes the production of isocyanates by carbamate cleavage at 150° C. to 350° C. in the presence of organic sulfonic acids of the type R¹SO₃H or salts thereof. R' here is an organic radical which may be substituted by groups that do not react with isocyanates, for example halogen, alkoxy or nitro groups. Specific examples mentioned are a number of aromatic (e.g. naphthalene-β-sulfonic acid) and aliphatic (e.g. methanesulfonic acid) sulfonic acids and also alkali metal salts of aromatic (sodium meta-xylene-4-sulfonate) and aliphatic (potassium methanesulfonate) sulfonic acids. Catalysts having a proton donor function and proton acceptor function within the meaning of the present invention are not disclosed. In particular, this application does not disclose using aromatic or araliphatic disulfonic acids or the monoanions of such disulfonic acids as catalysts.

The Japanese patent application JP 2011/162442 also deals with carbamate cleavage. Catalysts disclosed are the metal salts of non-coordinating anions. Non-coordinating anions disclosed are perfluoroalkylsulfonate, arylsulfonate, hexafluorophosphate, tetrafluoroborate, tetrakis(pentafluorophenyl)borate and also tetrakis[3,5-bis(trifluoromethyl)phenyl]borate. Preference is given to arylsulfonic acid anions, especially CH₃C₆H₄SO₃$^{(-)}$ (toluenesulfonate). Catalysts having an additional proton donor function are not disclosed. In particular, no disclosure of monoanions of aromatic or araliphatic disulfonic acids as suitable catalysts is provided.

The Korean application with the number 19930018854 (also published as KR970004412) describes the production of isocyanates R'—NCO from thionecarbamates and (stoichiometrically employed) halopyridinium salts in the presence of tertiary amines such as triethylamine, pyridine, quinoline, quinoxaline, hexamethylenetetramine, 1,4-diazabicyclo[2.2.2]octane, 1,5-diazabicyclo[4.3.0]non-5-ene and 1,8-diazabicylco[5.4.0]undec-7-ene according to the equation:

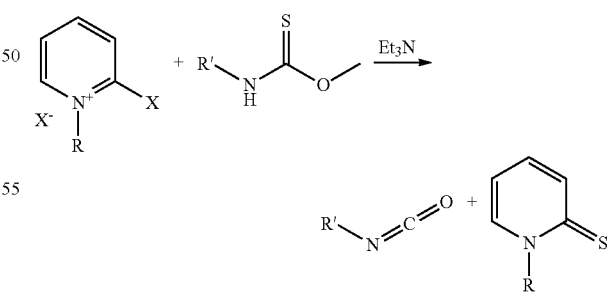

(X=F, Cl, I; R=alkyl radical; R'=aliphatic or aromatic radical)

The subject matter of the present invention, the formation of isocyanates by cleavage of carbamates or thiolcarbamates (which both have an —NH—(C═O) structural unit) with liberation of alcohols or thioalcohols, relates to a completely different chemical reaction. It is therefore not surprising that none of the tertiary amine catalysts disclosed in this document satisfies the conditions of a catalyst (X)(Y)(Z—H) of the present invention.

U.S. Pat. No. 4,081,472 describes conducting carbamate cleavages in the presence of metal ions of groups I-B, II-B, III-A, IV-A, IV-B, V—B and VIII, especially copper, zinc, aluminum, tin, titanium, vanadium, iron, cobalt and nickel ions. Said metal ions are used inter alia in the form of salts of carboxylic acids, in the form of alkoxides or thioalkoxides, in the form of phenoxides, salts of organic sulfonic acids, in the form of chelating complexes (by way of example of acetylacetonate) and in the form of salts of amino acids. Metal-free catalysts or catalysts containing metals at most as a catalytically inactive counterion are not disclosed in this document.

US 2016/0145201 A1 describes a multistage process for producing meta-xylidene diisocyanate in which inorganic acids such as sulfuric or phosphoric acid are used. The use of salts or organic esters of such acids as catalysts for the cleavage of carbamates is not disclosed in this document.

Despite advances in the field of phosgene-free isocyanate production in general and carbamate cleavage in particular, there is a continuing need for improvement in these phosgene-free synthesis routes. Although the carbamate cleavage can proceed uncatalyzed, suitable catalysts are still being sought which greatly accelerate the desired reaction without undesired side reactions and/or further reactions proceeding to a significant extent, that is to say which have a high selectivity for isocyanate formation.

SUMMARY

Taking this need into account, the present invention provides a process for producing an isocyanate in which a carbamate or thiolcarbamate is converted into the corresponding isocyanate at a temperature of at least 150° C. in the presence of a catalyst with elimination of an alcohol or thioalcohol, wherein the catalyst used is a compound of the general formula (X)(Y)(Z—H)

where:
(A)
X is $N(R^1)$,
Y is $C(R^2)$, a bridge formed of 2 carbon atoms which are part of a ring system composed of 5 or 7 carbon atoms with alternating double and single bonds, or is a bridge formed of 3, 5 or 7 carbon atoms with alternating single and double bonds, and
Z is O, S, $N(R^6)$ or $N^{(+)}(R^7)(R^8)$,
wherein the catalysts of type (A) have a $pK_B$ at 25° C. of ≥3.00;
or (B)
X is O,
—Y is $C(R^2)$, a bridge formed of 2 carbon atoms which are part of a ring system composed of 5 or 7 carbon atoms with alternating double and single bonds, or is a bridge formed of 3, 5 or 7 carbon atoms with alternating single and double bonds, and
Z is O;
or (C)
X is O,
Y is $S(O)(R^3)$ or $P(OR^4)(OR^5)$, and
Z is O;

where:
$R^1$ is
an optionally substituted aromatic or araliphatic radical having 6 to 10 carbon atoms or
an optionally substituted aliphatic radical having 1 to 6 carbon atoms or
joined to $R^2$ or $R^8$ to form a ring consisting of a total of 5 to 8 atoms, wherein the ring can optionally comprise heteroatoms, especially nitrogen and/or sulfur;
$R^2$ is
hydrogen or
an, optionally substituted, aromatic or araliphatic radical having 6 to 10 carbon atoms or
an, optionally substituted, aliphatic radical having 1 to 6 carbon atoms and optionally comprising ether units or
joined to $R^1$ or $R^6$ or $R^7$ to form a ring consisting of a total of 5 to 8 atoms, wherein the ring can optionally comprise heteroatoms, especially nitrogen and/or sulfur;
$R^3$ is
an aromatic or araliphatic radical having 6 to 10 carbon atoms which is substituted by a sulfonic acid group or sulfonate group or
an aliphatic radical having 1 to 6 carbon atoms which is substituted by an amine group, sulfonic acid group or sulfonate group or
$OHM^{(+)}$, where $M^{(+)}$ is an alkali metal cation, imidazolium cation, pyridinium cation, pyrrolidinium cation, phosphonium cation, sulfonium cation, $NH_4^+$, or is a mono-, di-, tri- or tetrasubstituted organic ammonium cation the organic substituents of which independently of one another are selected from the group consisting of methyl, ethyl, propyl, butyl, pentyl, hexyl, phenyl and cyclohexyl, where $M^{(+)}$ particularly preferably is an alkali metal cation or $NH_4^+$, very particularly preferably is an alkali metal cation selected from $Li^+$, $Na^+$ or $K^+$;
$R^4$ and $R^5$ independently of one another are
optionally substituted aromatic or araliphatic radicals each having 6 to 10 carbon atoms, where $R^4$ and $R^5$ may be joined to form a ring consisting of 5 to 8 atoms;
optionally substituted aliphatic radicals each having 1 to 6 carbon atoms, where $R^4$ and $R^5$ may be joined to form a ring consisting of 5 to 8 atoms;
$R^6$ is
an optionally substituted aromatic or araliphatic radical having 6 to 10 carbon atoms or
an optionally substituted aliphatic radical having 1 to 6 carbon atoms or
joined to $R^2$ to form a ring consisting of a total of 5 to 8 atoms, wherein the ring can optionally comprise heteroatoms, especially nitrogen and/or sulfur;
$R^7$ is
an optionally substituted aromatic or araliphatic radical having 6 to 10 carbon atoms or
an optionally substituted aliphatic radical having 1 to 6 carbon atoms or
joined to $R^2$ to form a ring consisting of a total of 5 to 8 atoms, wherein the ring can optionally comprise heteroatoms, especially nitrogen and/or sulfur;
$R^8$ is
an optionally substituted aromatic or araliphatic radical having 6 to 10 carbon atoms or
an optionally substituted aliphatic radical having 1 to 6 carbon atoms or joined to $R^1$ to form a ring consisting of a total of 5 to 8 atoms.

DETAILED DESCRIPTION

Carbamates which can be used according to the invention have the general formula R—NH—(C═O)—O—R', in which R and R¹ denote organic radicals (particularly preferred radicals R and R' are listed further below). According to the invention, thiolcarbamates (also referred to as thiolurethanes) are understood to be compounds of the type R—NH—(C═O)—S—R', in which an S-organyl group (S—R') is bonded to the carbon atom of the carbonyl group. (A distinction should be made between these and thionecarbamates (thioneurethanes) R—NH—(C═S)—O—R', in which in comparison to carbamates the oxygen atom of the carbonyl group has been replaced by sulfur. The label thiocarbamates (thiourethanes) is frequently used as a generic term for both substance classes.) In this respect, see also scheme 1 below.

Scheme 1: General structural formulae for carbamates (a), thiolcarbamates (b) and thionecarbamates (c).

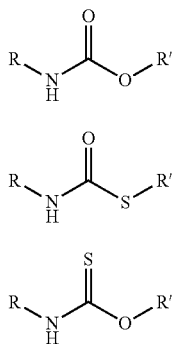

In the terminology of this invention, the terms carbamate and thiolcarbamate of course also encompass compounds having more than one, especially having two or more, carbamate or thiolcarbamate groups. Such further carbamate or thiolcarbamate groups are then part of the radical R of the structural formulae from scheme 1.

The catalysts mentioned feature both a proton donor function and a proton acceptor function. In the catalysts according to the invention, an abstractable proton (H⁺) is bonded to a heteroatom which is more electronegative than carbon. This heteroatom is either identical to Z (Z═O:Z—H═.O—H) or is a constituent thereof (e.g. the nitrogen atom when Z═N(R⁶):Z—H═C₆H₅(N.)H). A proton acceptor function which is either identical to X (X═O) or is a constituent thereof (e.g. the nitrogen atom when X═N(R'): X═C₆H₅—N:) is further present in the catalysts according to the invention. According to the invention, (X) and "Z" in (Z—H) are covalently connected to one another via (Y). This connection can be realized by a bridge formed of 2 carbon atoms or by a bridge formed of 3, 5 or 7 carbon atoms with alternating single and double bonds. The connection can also be realized by a single carbon atom ((Y)═C(R²)).

An example of a catalyst of type (A) is

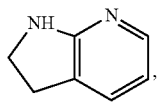

having a pK$_B$ of 3.25, in which: Z═N(R⁶), Y═C(R²) and X═N(R¹), where firstly R¹ and R² are joined to form a ring of 6 atoms which contains the heteroatom N (namely the "pyridine" nitrogen), and secondly R⁶ and R² are joined to form a ring of 5 atoms which contains the heteroatom N (namely the nitrogen bearing the proton). In this example, the five- and the six-membered ring share two carbon atoms; this is expressly encompassed by the invention (but of course is not mandatory). Further, in this example the carbon atom in C(R²) is part both of the ring that is formed by the joining of R¹ and R² and of the ring that is formed by the joining of R⁶ and R²; this too is expressly encompassed by the invention. Within the context of this invention, the pK$_B$ values calculated according to *Advanced Chemistry Development (ACD/Labs) Software V*11.02 for 25° C. are considered to be definitive. These have been tabulated for numerous organic compounds and are accessible via the substance search of the Chemical Abstracts Service SCIFINDER® database under *Substance Detail, Predicted Properties, Chemical*. In the case of compounds of type (A) having a plurality of basic groups, the inventive requirement of a minimum pK$_B$ of 3.00 has to be satisfied by the most strongly basic group.

A further example of a catalyst of type (A) is

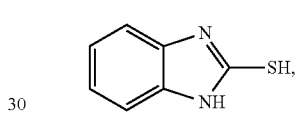

in which Z═S, Y═C(R²), X═N(R¹), with R¹ being joined to R² to form a ring consisting of 5 atoms (the imidazole ring). In this example, the imidazole ring resulting from the joining of R¹ and R² is fused with a benzene ring; this is expressly encompassed by the invention.

An example of a catalyst of type (B) is

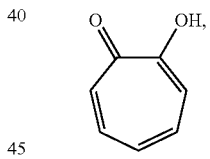

in which: Z═O, Y=bridge formed of 2 carbon atoms which are part of a ring system of 7 carbon atoms with alternating single and double bonds, and X═O.

An example of a catalyst of type (C) is

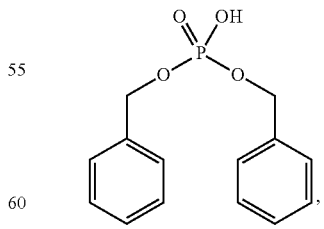

in which: Z═O, Y═P(OR⁴)(OR⁵) and X═O, where in addition R⁴ and R⁵ are araliphatic radicals each having 7 carbon atoms.

Without wishing to be bound to a theory, it is assumed that the presence of proton donor function and proton acceptor function in the same molecule permits a proton shift which is essential for the carbamate or thiolcarbamate cleavage. This is also supported by the fact that the catalysts mentioned can be formally represented in structural formulae in which the proton donor function and proton acceptor function are linked by alternating atom-atom single bonds and atom-atom double bonds.

There firstly follows a brief summary of various possible embodiments of the invention:

In a first embodiment of the invention, which can be combined with all other embodiments, the conversion of the starting carbamate or starting thiolcarbamate is conducted in solution in the presence of an organic solvent selected from aprotic polar solvents without isocyanate-reactive groups.

In a second embodiment of the invention, which is a particular configuration of the first embodiment, the organic solvent is selected from diphenyl ether, sulfolane, cyclic propylene carbonate or an ionic liquid (especially 1-butyl-3-methylimidazolium hydrogensulfate, 1-butyl-3-methylimidazolium methanesulfonate and/or trihexyltetradecylphosphonium bis(2,4,4-trimethylpentyl)phosphinate).

In a third embodiment of the invention, which is a particular configuration of the first and second embodiments, a concentration of the starting carbamate or starting thiolcarbamate in the solution is set in the range from 5% by mass to 95% by mass, preferably in the range from 10% by mass to 20% by mass, based on the total mass of the solution.

In a fourth embodiment of the invention, which can be combined with all other embodiments, a molar ratio of starting carbamate or starting thiolcarbamate to catalyst of 1000:1 to 1:1, preferably of 100:1 to 10:1, is used.

In a fifth embodiment of the invention, which can be combined with all other embodiments, the conversion is conducted at a temperature in the range from 150° C. to 280° C. and at a pressure in the range from 0.001 $bar_{(abs.)}$ to 2.00 $bar_{(abs.)}$, particularly preferably at a temperature in the range from 160° C. to 260° C. and at a pressure in the range from 0.001 $bar_{(abs.)}$ to 1.00 $bar_{(abs.)}$, very particularly preferably at a temperature in the range from 180° C. to 240° C. and at a pressure in the range from 0.001 $bar_{(abs.)}$ to 1.00 $bar_{(abs.)}$.

In a sixth embodiment of the invention, which can be combined with all other embodiments, the conversion is conducted continuously or discontinuously in a reactor selected from the group consisting of stirred tanks, stirred tank cascades, distillation columns and tubular reactors.

In a seventh embodiment of the invention, which is a particular configuration of the sixth embodiment, a residence time of the reaction mixture in the reactor is set in the range from 0.5 h to 10 h, preferably in the range from 1.0 h to 8.0 h, particularly preferably in the range from 1.5 h to 6.0 h.

In an eighth embodiment of the invention, which can be combined with all other embodiments, the isocyanate formed and/or the alcohol or thioalcohol formed is removed from the reaction mixture continuously or at intervals.

In a ninth embodiment of the invention, which is a particular configuration of the eighth embodiment, the alcohol or thioalcohol formed is removed from the reaction mixture continuously or at intervals, wherein the removal of the alcohol or thioalcohol is effected by passing through a stripping gas (preferably nitrogen or a noble gas such as in particular helium or argon) and/or by distillation, optionally assisted by application of a pressure which is reduced compared to ambient pressure.

In a tenth embodiment of the invention, which is a further particular configuration of the eighth embodiment, the isocyanate formed and the alcohol or thioalcohol formed are removed from the reaction mixture continuously or at intervals, wherein either (i) both are removed together, followed by a separation of the gaseous mixture obtained containing the isocyanate and the alcohol or thioalcohol by means of fractional condensation, or (ii) first the alcohol or thioalcohol and then the isocyanate is removed from the reaction mixture. The removal of the isocyanate formed is advantageously effected by distillation; in the case of variant (i) the isocyanate formed and the alcohol or thioalcohol formed are in this case distilled off from the reaction mixture together, wherein the distillation may be assisted by passing through a stripping gas (preferably nitrogen or a noble gas such as in particular helium or argon). In the case of variant (ii) the removal of the alcohol or thioalcohol can be effected by passing through a stripping gas (preferably nitrogen or a noble gas such as in particular helium or argon) and/or by distillation; the removal of the isocyanate is preferably effected by distillation, with the passing through of a stripping gas (preferably nitrogen or a noble gas such as in particular helium or argon) being able to be used to assist, however.

In an eleventh embodiment of the invention, which is a particular configuration of the tenth embodiment, the reaction mixture is distilled continuously in two series-connected distillation columns in order to remove the alcohol or thioalcohol and the isocyanate.

In a twelfth embodiment of the invention, which can be combined with all other embodiments, the isocyanate to be produced is butylene 1,4-diisocyanate, pentane 1,5-diisocyanate, hexamethylene 1,6-diisocyanate or the dimers, trimers, pentamers, heptamers or nonamers thereof or mixtures of same, isophorone diisocyanate, 2,2,4- and/or 2,4,4-trimethylhexamethylene diisocyanate, the isomeric bis (4,4'-isocyanatocyclohexyl)methanes or mixtures thereof in any desired proportions, cyclohexylene 1,4-diisocyanate, phenyl isocyanate, phenylene 1,4-diisocyanate, tolylene 2,4- and/or 2,6-diisocyanate, naphthylene 1,5-diisocyanate, diphenylmethane 2,2'- and/or 2,4'- and/or 4,4'-diisocyanate and/or the higher homologs thereof, 1,3- and/or 1,4-bis(2-isocyanatoprop-2-yl)benzene, 1,3-bis(isocyanatomethyl)benzene, or an alkyl 2,6-diisocyanatohexanoate (lysine diisocyanate) having alkyl groups of 1 carbon atom to 6 carbon atoms, and the carbamate or thiolcarbamate used is the methyl, ethyl, n-propyl, isopropyl, n-butyl, isobutyl, tert-butyl, cyclohexyl or phenyl carbamate or thiolcarbamate or substituted methyl, ethyl, n-propyl, isopropyl, n-butyl, isobutyl, tert-butyl, cyclohexyl or phenyl carbamate or thiolcarbamate which corresponds to the isocyanate to be produced.

In a thirteenth embodiment of the invention, which can be combined with all other embodiments, no further catalyst is used besides the catalyst (X)(Y)(Z)H.

In a fourteenth embodiment of the invention, which can be combined with all other embodiments, the catalyst (X)(Y)(Z—H) is selected from the group consisting of 2-hydroxy-2,4,6-cycloheptatrien-1-one (tropolone) (a); 2-acetyl-1-tetralone (b); N,N'-diphenylformamidine (c); N-(2,6-dimethylphenyl)-5,6-dihydro-4H-1,3-thiazin-2-amine (xylazine) (d); 2,3-dihydro-7-azaindole (e); protonated N-methyl-1,5,7-tri azabicyclo[4.4.0] dec-5-ene (f); protonated 1,8-diazabicyclo[5.4.0]undec-7-ene (g); O-methyl-N,N'-diisopropylisourea (h); 2-mercaptopyridine (i); 1,3,4-thiadiazole-2,5-dithiol (j); mercaptobenzimidazole (k); the constitutional isomers of the benzenedisulfonic acid monoanion (l); the constitutional isomers of benzenedisulfonic acid (m); (R)-(−)-1,1'-binaphthyl-2,2'-hydrogenphosphate (n); dibenzyl hydrogenphosphate (o); naphthalene-2,6-disulfonic acid monoanion (p); alkali metal hydrogensulfate (q); 2-aminoethane-1-sulfonic acid (taurine) (r) and mixtures (s) of the compounds mentioned.

In a fifteenth embodiment of the invention, which can be combined in particular (but not only) with the fourteenth embodiment, the catalysts used are those of type (A), preferably exclusively those of type (A).

In a seventeenth embodiment of the invention, which can be combined in particular (but not only) with the fourteenth embodiment, the catalysts used are those of type (B), preferably exclusively those of type (B).

In an eighteenth embodiment of the invention, which can be combined in particular (but not only) with the fourteenth embodiment, the catalysts used are those of type (C), preferably exclusively those of type (C).

The embodiments briefly outlined above and further possible configurations of the invention are elucidated in more detail hereinafter. Various embodiments are combinable with one another as desired unless the opposite is clearly apparent to those skilled in the art from the context.

Starting carbamates usable according to the invention can be obtained via various routes known per se. Examples include the transesterification of N-arylurea derivatives with alcohols (described for example in J. Wang et al., *Applied Catalysis A: General*, 2004, 261, 191-197), the reductive carbonylation of nitroaromatics with carbon monoxide and alcohols (described for example in M. vGasperini et al., *Adv. Syn. Cat.*, 2005, 347, 105-120), the oxidative carbonylation of amines with carbon monoxide and oxygen (described for example in S. Fukuoka, M. Chono, M. Kohno, *J. Chem. Soc., Chem. Commun.*, 1984, 399) and the reaction of primary amines with organic carbonates (described for example in U.S. Pat. No. 8,871,965 B2).

According to the invention, preference is given to the reaction of primary amines with organic carbonates, which proceeds according to

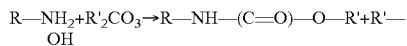
R—NH$_2$+R'$_2$CO$_3$→R—NH—(C=O)—O—R'+R'—OH

Preference is given to using processes such as are described for example in WO 2014/187756 A1 and the literature references cited therein. These reactions are catalyzed for example by zinc clusters, zinc salts or Lewis acids.

Starting thiolcarbamates usable according to the invention can be obtained via various routes known per se. Examples from the specialist literature have been disclosed for example in Tetrahedron 50 (1994) 5669-5680, Tetrahedron 59 (2003) 1327-1331, Tetrahedron 60 (2004) 2869-2873, Tetrahedron 61 (2005) 7153-7175, J. Org. Chem. 68 (2003) 3733-3735, J. Org. Chem. 70 (2005) 2551-2554 and U.S. Pat. No. 4,486,449. Starting thiolcarbamates usable according to the invention are particularly preferably obtained by the carbonylation of amines with carbon monoxide, sulfur and alkyl halides.

The conversion of the starting carbamate or starting thiolcarbamate is preferably conducted in solution. Suitable solvents are especially aprotic polar solvents without isocyanate-reactive groups. Preference is given to diphenyl ether, sulfolane, cyclic propylene carbonate or ionic liquids (especially 1-butyl-3-methylimidazolium hydrogensulfate, 1-butyl-3-methylimidazolium methanesulfonate and/or trihexyltetradecylphosphonium bis(2,4,4-trimethylpentyl)phosphinate). The concentration of the starting carbamate or starting thiolcarbamate in the solution is preferably in the range from 5% by mass to 95% by mass, particularly preferably in the range from 10% by mass to 20% by mass, based on the total mass of the solution. Preference is given to using a molar ratio of starting carbamate or starting thiolcarbamate to catalyst of 1000:1 to 1:1, preferably of 100:1 to 10:1. However, a solvent-free synthesis is also possible.

The process according to the invention is preferably performed at a temperature in the range from 150° C. to 280° C. and at a pressure in the range from 0.001 bar$_{(abs.)}$ to 2.00 bar$_{(abs.)}$, particularly preferably at a temperature in the range from 160° C. to 260° C. and at a pressure in the range from 0.001 bar$_{(abs.)}$ to 1.00 bar$_{(abs.)}$, very particularly preferably at a temperature in the range from 180° C. to 240° C. and at a pressure in the range from 0.001 bar$_{(abs.)}$ to 1.00 bar$_{(abs.)}$. The process according to the invention can be carried out either continuously or discontinuously ("batchwise"). Suitable reactors for performing the process are especially stirred tanks or stirred tank cascades, distillation columns (reactive distillation) or tubular reactors. The residence time of the reaction mixture in the reactor used is in this case preferably from 0.5 h to 10 h, particularly preferably from 1.0 h to 8.0 h, very particularly preferably from 1.5 h to 6.0 h.

It is particularly preferable to remove the isocyanate formed and/or the alcohol or thioalcohol formed from the reaction mixture continuously or at intervals. This can be effected by passing through a stripping gas (preferably nitrogen or a noble gas such as in particular helium or argon) and/or by distillation, optionally assisted by application of a pressure which is reduced compared to ambient pressure. In particular in the case of distillation, the conditions can be selected here such that both are distilled off together. In this case it is preferable to separate the mixture distilled off, obtained in gaseous form and containing the isocyanate to be produced and the alcohol or thioalcohol (and also any low-boiling secondary components) in two or more steps by fractional condensation, and in this way to obtain the isocyanate and the alcohol or thioalcohol.

It is also conceivable to remove only the lower-boiling component (generally the alcohol or thioalcohol) from the reaction mixture (less preferred), or to first remove the lower-boiling and then the higher-boiling (more preferred). In a continuous mode of operation, the last-mentioned variant can be realized in the simplest case by connecting two distillation columns in series. In the case of polycarbamates or polythiolcarbamates, it should be ensured that the corresponding polyisocyanate (usually a diisocyanate) is only distilled off once all carbamate or thiolcarbamate groups of the starting compound have been converted into isocyanate groups (unless the target product were a mixed (thiolo)carbamate isocyanate, which generally however will not be the case).

Suitable carbamates are in particular those carbamates that can be traced back retrosynthetically to the reaction of
(1) primary, secondary or tertiary (optionally substituted) aliphatic monoalcohols R—OH' such as
methanol, ethanol, n-propanol, isopropanol, n-butanol, isobutanol, tert-butanol, the higher homologs thereof, cyclohexanol, with the primary monoalcohols being preferred, or (optionally substituted) phenol
with
(2) isocyanates R—NCO such as
butylene 1,4-diisocyanate, pentane 1,5-diisocyanate (PDI), hexamethylene 1,6-diisocyanate (HDI) or the dimers, trimers, pentamers, heptamers or nonamers thereof or mixtures of same, isophorone diisocyanate (IPDI), 2,2,4- and/or 2,4,4-trimethylhexamethylene diisocyanate, the isomeric bis(4,4'-isocyanatocyclohexyl)methanes or mixtures thereof in any desired proportions, cyclohexylene 1,4-diisocyanate, phenyl isocyanate, phenylene 1,4-diisocyanate, tolylene 2,4- and/or 2,6-diisocyanate (TDI), naphthylene 1,5-diisocyanate, diphenylmethane 2,2'- and/or 2,4'- and/or 4,4'-diisocyanate (MDI) and/or higher homologs (polymeric MDI), 1,3- and/or 1,4-bis(2-isocyanatoprop-2-yl)benzene (TMXDI), 1,3-bis(isocyanatomethyl)benzene (XDI), and also alkyl 2,6-diisocyanatohexanoates (lysine diisocyanates) having alkyl groups of 1 carbon atom to 6 carbon atoms.

Suitable thiolcarbamates are in particular compounds that can be traced back retrosynthetically to the reaction of the monothioalcohols R'—SH (1'-replacement of O by S) corresponding to the previously mentioned monoalcohols (1) with the mentioned isocyanates (2). Particular preference is given here to thiomethanol, thioethanol, thioisopropanol and (optionally substituted) thiophenol.

In the formulae R—NH—(C=O)—O—R' and R—NH—(C=O)—S—R', R therefore corresponds to the radical of the isocyanate (that is to say e.g. $C_6H_5$ in the case of phenyl isocyanate; in the case of isocyanates having more than one isocyanate group the corresponding carbamate also has the appropriate number of carbamate functions R'—O—(CO)—NH—) and $R^1$ corresponds to the radical of the monoalcohol (e.g. $CH_3$ in the case of methanol).

In the case of substituted alkyl carbamates or alkyl thiolcarbamates (R—NH—(CO)—O—R'), the aliphatic radical $R^1$ bears substituents which independently of one another are selected from the group consisting of CN, $NO_2$, F, Cl, Br, I, OR", where R" is an alkyl group, especially is $CH_3$, $C_2H_6$, n-$C_3H_7$, n-$C_4H_9$, i-$C_4H_9$, t-$C_4H_9$, n-$C_5H_{11}$; or n-$C_6H_{13}$, and R has the same meaning as above. Here, at least one hydrogen atom of the aliphatic radical $R^1$ has been replaced by one of the mentioned substituents.

In the case of substituted phenyl carbamates (R—NH—(CO)—O—$C_6H_{m-5}A_m$) or phenyl thiolcarbamates (R—NH)—(CO)—S—$C_6H_{m-5}A_m$), the aromatic six-membered ring bears up to m substituents A which independently of one another are selected from the group consisting of CN, $NO_2$, F, Cl, Br, I, OH, COOH, COCl, COOR", OR", $CH_3$, $C_2H_6$, n-$C_3H_7$, iso-$C_3H_7$, where m is a natural number in the range from 0 to 5, preferably from 0 to 4, particularly preferably from 0 to 1, and R" is an alkyl group, especially is $CH_3$, $C_2H_6$, n-$C_3H_7$, iso-$C_3H_7$, n-$C_4H_9$, iso-$C_4H_9$, tert-$C_4H_9$, n-$O_5H_{11}$ or n-$C_6H_{13}$, and R has the same meaning as above.

In all embodiments of the invention, it is preferable not to use any other catalysts besides the catalyst (X)(Y)(Z)H. The process according to the invention thus makes it possible—apart from a possibly used metallic cation in the case of salt-type catalysts—to completely dispense with metal-containing catalysts, which has the advantage that the process as a whole becomes more environmentally friendly and requires a less complicated workup of the crude product. This means both that a less intense purification of the product is necessary since catalyst residues are less toxic and thus can remain in the product and also that resulting waste can be disposed of more simply. In addition, the use of metals, especially in the region of the nobler metals, that is customary in the prior art is often associated with high costs.

In addition to the catalyst structures (X)(Y)(Z)H themselves, the conversion products thereof formed under reaction conditions may also be catalytically active.

The catalyst (X)(Y)(Z)H is preferably selected from the group consisting of (see also scheme 2 below) 2-hydroxy-2,4,6-cycloheptatrien-1-one (tropolone) (a); 2-acetyl-1-tetralone (b); shown below in the "enol form"; N,N'-diphenylformamidine (c; pKB=6.30); N-(2,6-dimethylphenyl)-5,6-dihydro-4H-1,3-thiazin-2-amine (xylazine) (d; pKB=6.33); 2,3-dihydro-7-azaindole (e; pKB=3.25); protonated N-methyl-1,5,7-triazabicyclo[4.4.0]dec-5-ene (f); protonated 1,8-diazabicyclo[5.4.0]undec-7-ene (g); O-methyl-N,N'-diisopropylisourea (h; $pK_B$=4.15); 2-mercaptopyridine (i; pKB=4.24); 1,3,4-thiadiazole-2,5-dithiol (j; pKB=8.34); mercaptobenzimidazole (k); the constitutional isomers of the benzenedisulfonic acid monoanion (=sulfobenzenesulfonate) (l); the constitutional isomers of benzenedisulfonic acid (m); (R)-(−)-1,1'-binaphthyl-2,2'-hydrogenphosphate (n); dibenzyl hydrogenphosphate (o); naphthalene-2,6-disulfonic acid monoanion (p); alkali metal hydrogensulfate (q), 2-aminoethane-1-sulfonic acid (taurine) (r) and mixtures (s) of the compounds mentioned. For the protonated compounds (salts) (f) and (g), no $pK_B$ values are documented in the literature as of the current state of knowledge; however it will be apparent to those skilled in the art that these compounds satisfy the inventive criterion ($pK_B$≥3.00), since both are already protonated and thus have an extremely low tendency to accept a further proton (and therefore the $pK_B$ is higher compared to the unprotonated species).

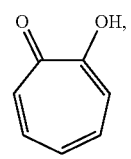

(a)

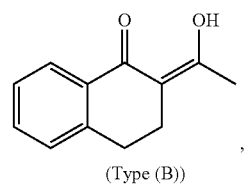

(Type (B))

(b)

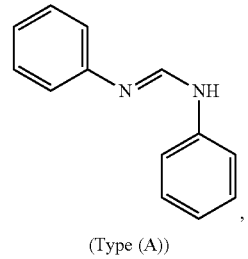

(Type (B))

(c)

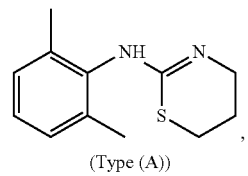

(Type (A))

(d)

(Type (A))

-continued

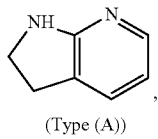

(Type (A))

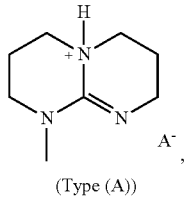

(Type (A))

where A⁻ is a non-nucleophilic anion, in particular selected from the group consisting of tosylate, bis(trifluoromethylsulfonyl)imide, tert-butoxide, diisopropylamide, hexafluorophosphate, tetrafluoroborate, perchlorate and tetrakis[3,5-bis(trifluoromethyl)phenyl]borate ("BARF"),

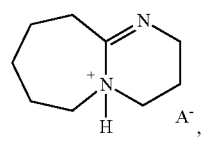

(Type (A))

where A⁻ has the definition given previously,

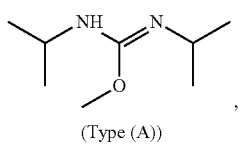

(Type (A))

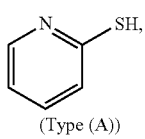

(Type (A))

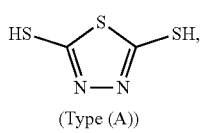

(Type (A))

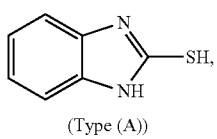

(Type (A))

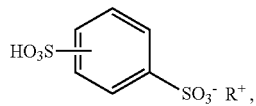

(Type (C))

where $R^{(+)}$ is a cation, preferably an alkali metal cation, imidazolium cation, pyridinium cation, pyrrolidinium cation, phosphonium cation, sulfonium cation, $NH_4^+$ or is a mono-, di-, tri- or tetrasubstituted organic ammonium cation the organic substituents of which independently of one another are selected from the group consisting of methyl, ethyl, propyl, butyl, pentyl, hexyl, phenyl and cyclohexyl, where $R^{(+)}$ particularly preferably is an alkali metal cation or $NH_4^+$, very particularly preferably is an alkali metal cation selected from $Li^+$, $Na^+$, or $K^+$,

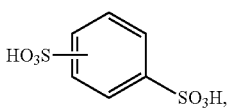

(Type (C))

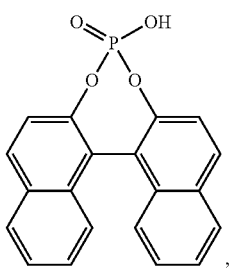

(Type (C))

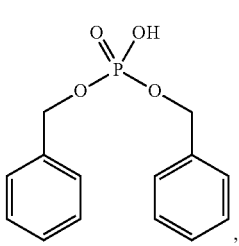 [SMILES: O=P(O)(OCc1ccccc1)OCc1ccccc1]

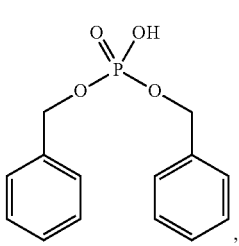 [SMILES: O=P(O)(OCc1ccccc1)OCc1ccccc1]

(Type (C))

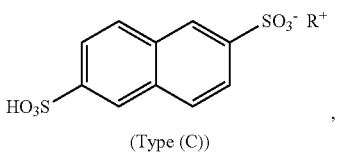

(Type (C))

where $R^{(+)}$ has the definition given previously,

-continued

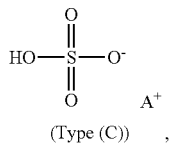

(Type (C)), where A⁺ is an alkali metal cation, in particular is Na⁺,

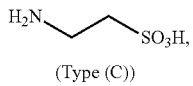

(Type (C))

and mixtures of the aforementioned compounds.

In one embodiment of the invention, catalysts of type (A) are used, in particular exclusively those of type (A). Particular preference is given here to the catalysts of type (A) mentioned in scheme 2.

In another embodiment of the invention, catalysts of type (B) are used, in particular exclusively those of type (B). Particular preference is given here to the catalysts of type (B) mentioned in scheme 2.

In one embodiment of the invention, catalysts of type (C) are used, in particular exclusively those of type (C). Particular preference is given here to the catalysts of type (C) mentioned in scheme 2.

Of the catalysts mentioned in scheme 2, very particular preference is given to alkali metal hydrogensulfate (especially sodium hydrogensulfate) (q)), and benzene-1,3-disulfonic acid monoanion (3-sulfobenzenesulfonate) (1) (both of type (C)).

Catalysts usable according to the invention are commercially available or at least obtainable by known methods. For instance, catalysts in protonated form ((f) and (g)) are obtainable for example by reacting the neutral form with the acid A-H, by way of example trifluoromethanesulfonic acid. The compounds (1) and (p) can for example be obtained by reacting the corresponding dianions, for example the disodium salts, with an acid such as in particular sulfuric acid or trifluoromethanesulfonic acid.

The invention will be elucidated in yet more detail below on the basis of examples.

EXAMPLES

The experiments were performed in standard laboratory apparatuses. The reaction vessels were inertized with argon. Phenanthrene was used as an internal standard for quantitative HPLC analysis.

Example 1: Conversion of Methyl N-Phenylcarbamate into Phenyl Isocyanate by Thermal Cleavage at 200° C. in Diphenyl Ether (Comparative Example without Catalyst)

In an inertized multi-neck flask, 0.61 g (3.42 mmol) of phenanthrene were dissolved in 29.34 g (172.38 mmol) of diphenyl ether. The reaction mixture was heated to 215° C. In an inertized Schlenk tube, 4.97 g (32.88 mmol) of methyl N-phenylcarbamate were heated to 150° C. Completely transferring the methyl N-phenylcarbamate into the reaction mixture resulted in a mixture having a temperature of 200° C. This temperature was held constant for 120 minutes. The gaseous reaction products formed were driven out at an argon inert gas flow of 10 l/h and collected in a cold trap. The progress of the reaction was monitored by means of continuous sampling from the reaction vessel and subsequent analysis by means of $^1$H NMR spectroscopy.

The yield of phenyl isocyanate was 20% with a selectivity of 91%.

Example 2: Conversion of Methyl N-Phenylcarbamate into Phenyl Isocyanate by Thermal Cleavage at 200° C. in Sulfolane (Comparative Example without Catalyst)

In an inertized multi-neck flask, 0.75 g (4.21 mmol) of phenanthrene were dissolved in 25.14 g (209.20 mmol) of sulfolane. The reaction mixture was heated to 217° C. In an inertized Schlenk tube, 6.35 g (42.01 mmol) of methyl N-phenylcarbamate were heated to 150° C. Completely transferring the methyl N-phenylcarbamate into the reaction mixture resulted in a mixture having a temperature of 200° C. This temperature was held constant for 120 minutes. The gaseous reaction products formed were driven out at an argon inert gas flow of 10 l/h and collected in a cold trap. The progress of the reaction was monitored by means of continuous sampling from the reaction vessel and subsequent analysis by means of $^1$H NMR spectroscopy.

The yield of phenyl isocyanate was 17% with a selectivity of 87%.

Example 3: Conversion of Methyl N-Phenylcarbamate into Phenyl Isocyanate by Cleavage at 60° C. in the Presence of Sodium 3-Sulfobenzenesulfonate at a Molar Ratio of Carbamate to Catalyst of 19.5:1 (Comparative Example at Excessively Low Temperature for the Catalyst Concentration Chosen)

In an inertized multi-neck flask, 0.59 g (3.31 mmol) of phenanthrene and also 0.65 g (1.71 mmol) of sodium 3-sulfobenzenesulfonate were suspended in 30.01 g (176.31 mmol) of diphenyl ether. 5.03 g (33.27 mmol) of methyl N-phenylcarbamate were added to this reaction mixture and heated to 60° C. This temperature was held constant for 120 minutes. The gaseous reaction products formed were driven out at an argon inert gas flow of 10 l/h and collected in a cold trap. The progress of the reaction was monitored by means of continuous sampling from the reaction vessel and subsequent analysis by means of NMR spectroscopy.

No isocyanate formation could be observed.

Example 4: Conversion of Methyl N-Phenylcarbamate into Phenyl Isocyanate by Cleavage at 200° C. in the Presence of Sodium 3-Sulfobenzenesulfonate (Catalyst of Type (C)) at a Molar Ratio of Carbamate to Catalyst of 21.3:1

In an inertized multi-neck flask, 0.60 g (3.37 mmol) of phenanthrene and also 0.59 g (1.55 mmol) of sodium 3-sulfobenzenesulfonate were suspended in 30.01 g (176.31 mmol) of diphenyl ether. The reaction mixture was heated to 215° C. In an inertized Schlenk tube, 4.99 g (33.01 mmol) of methyl N-phenylcarbamate were heated to 150° C. Completely transferring the methyl N-phenylcarbamate into the reaction mixture resulted in a mixture having a temperature of 200° C. This temperature was held constant for 120 minutes. The gaseous reaction products formed were driven out at an argon inert gas flow of 10 l/h and collected in a cold trap. The progress of the reaction was monitored by means of continuous sampling from the reaction vessel and subsequent analysis by means of NMR spectroscopy.

The yield of phenyl isocyanate was 32% with a selectivity of 74%.

Example 5: Conversion of Methyl N-Phenylcarbamate into Phenyl Isocyanate by Cleavage at 240° C. in the Presence of Sodium 3-Sulfobenzenesulfonate (Catalyst of Type (C)) at a Molar Ratio of Carbamate to Catalyst of 19.5:1

In an inertized multi-neck flask, 0.60 g (3.37 mmol) of phenanthrene and also 0.66 g (1.74 mmol) of sodium 3-sulfobenzenesulfonate were suspended in 30.11 g (176.90 mmol) of diphenyl ether. The reaction mixture was heated to 261° C. In an inertized Schlenk tube, 5.13 g (33.94 mmol) of methyl N-phenylcarbamate were heated to 178° C. Completely transferring the methyl N-phenylcarbamate into the reaction mixture resulted in a mixture having a temperature of 240° C. This temperature was held constant for 120 minutes. The gaseous reaction products formed were driven out at an argon inert gas flow of 10 l/h and collected in a cold trap. The progress of the reaction was monitored by means of continuous sampling from the reaction vessel and subsequent analysis by means of NMR spectroscopy.

The yield of phenyl isocyanate was 68% with a selectivity of 69%.

Example 6: Conversion of Methyl N-Phenylcarbamate into Phenyl Isocyanate by Cleavage at 200° C. in the Presence of Sodium 3-Sulfobenzenesulfonate (Catalyst of Type (C)) at a Molar Ratio of Carbamate to Catalyst of 1.01:1

In an inertized multi-neck flask, 0.50 g (2.81 mmol) of phenanthrene and also 9.99 g (26.26 mmol) of sodium 3-sulfobenzenesulfonate were suspended in 25.02 g (146.99 mmol) of diphenyl ether. The reaction mixture was heated to 215° C. In an inertized Schlenk tube, 4.01 g (26.53 mmol) of methyl N-phenylcarbamate were heated to 150° C. Completely transferring the methyl N-phenylcarbamate into the reaction mixture resulted in a mixture having a temperature of 200° C. This temperature was held constant for 120 minutes. The gaseous reaction products formed were driven out at an argon inert gas flow of 10 l/h and collected in a cold trap. The progress of the reaction was monitored by means of continuous sampling from the reaction vessel and subsequent analysis by means of NMR spectroscopy.

The yield of phenyl isocyanate was 69% with a selectivity of 81%.

Example 7: Conversion of Methyl N-Phenylcarbamate into Phenyl Isocyanate by Cleavage at 200° C. in the Presence of N,N'-Diphenylformamidine (Catalyst of Type (A)) at a Molar Ratio of Carbamate to Catalyst of 19.1:1

In an inertized multi-neck flask, 0.81 g (4.54 mmol) of phenanthrene and also 0.44 g (2.24 mmol) of N,N'-diphenylformamidine were dissolved in 25.35 g (148.93 mmol) of diphenyl ether. The reaction mixture was heated to 216° C. In an inertized Schlenk tube, 6.48 g (42.87 mmol) of methyl N-phenylcarbamate were heated to 150° C. Completely transferring the methyl N-phenylcarbamate into the reaction mixture resulted in a mixture having a temperature of 200° C. This temperature was held constant for 120 minutes. The gaseous reaction products formed were driven out at an argon inert gas flow of 10 l/h and collected in a cold trap. The progress of the reaction was monitored by means of continuous sampling from the reaction vessel and subsequent analysis by means of NMR spectroscopy.

The yield of phenyl isocyanate was 32% with a selectivity of 84%.

Example 8: Conversion of Dimethyl Toluene-2,4-Dicarbamate into Toluene 2,4-Diisocyanate by Cleavage at 200° C. in the Presence of Sodium 3-Sulfobenzenesulfonate (Catalyst of Type (C)) at a Molar Ratio of Carbamate to Catalyst of 10.1:1

In an inertized multi-neck flask, 0.62 g (3.48 mmol) of phenanthrene and also 1.27 g (3.34 mmol) of sodium 3-sulfobenzenesulfonate were suspended in 30.42 g (178.72 mmol) of diphenyl ether. To the reaction mixture were added 8.02 g (33.66 mmol) of dimethyl toluene-2,4-dicarbamate and the mixture was heated to 200° C. This temperature was held constant for 120 minutes. The gaseous reaction products formed were driven out at an argon inert gas flow of 10 l/h and collected in a cold trap. The progress of the reaction was monitored by means of continuous sampling from the reaction vessel and subsequent analysis by means of $^1$H NMR spectroscopy.

The yield of toluene 2,4-diisocyanate was 50% with a selectivity of 86%.

Example 9: Conversion of Methyl N-Octylcarbamate into n-Octyl Isocyanate by Cleavage at 200° C. in the Presence of Sodium 3-Sulfobenzenesulfonate (Catalyst of Type (C)) at a Molar Ratio of Carbamate to Catalyst of 19.5:1

In an inertized multi-neck flask, 0.49 g (2.75 mmol) of phenanthrene and also 0.52 g (1.37 mmol) of sodium 3-sulfobenzenesulfonate were suspended in 25.30 g (148.64 mmol) of diphenyl ether. The reaction mixture was heated to 215° C. In an inertized Schlenk tube, 5.00 g (26.70 mmol) of methyl N-octylcarbamate were heated to 150° C. Completely transferring the methyl N-octylcarbamate into the reaction mixture resulted in a mixture having a temperature of 200° C. This temperature was held constant for 120 minutes. The gaseous reaction products formed were driven out at an argon inert gas flow of 10 l/h and collected in a cold trap. The progress of the reaction was monitored by means of continuous sampling from the reaction vessel and subsequent analysis by means of NMR spectroscopy.

The yield of n-octyl isocyanate was 31% with a selectivity of 84%.

Example 10: Conversion of Methyl N-Phenylcarbamate into Phenyl Isocyanate by Cleavage at 200° C. in the Presence of Tropolone (Catalyst of Type (B)) at a Molar Ratio of Carbamate to Catalyst of 18.0:1

In an inertized multi-neck flask, 0.60 g (3.37 mmol) of phenanthrene and also 0.23 g (1.88 mmol) of tropolone were dissolved in 25.78 g (151.46 mmol) of diphenyl ether. The reaction mixture was heated to 215° C. In an inertized Schlenk tube, 5.11 g (33.80 mmol) of methyl N-phenylcarbamate were heated to 150° C. Completely transferring the methyl N-phenylcarbamate into the reaction mixture resulted in a mixture having a temperature of 200° C. This temperature was held constant for 120 minutes. The gaseous reaction products formed were driven out at an argon inert gas flow of 10 l/h and collected in a cold trap. The progress of the reaction was monitored by means of continuous sampling from the reaction vessel and subsequent analysis by means of NMR spectroscopy.

The yield of phenyl isocyanate was 19% with a selectivity of 86%.

Example 11: Conversion of Methyl N-Phenylcarbamate into Phenyl Isocyanate by Cleavage at 200° C. in the Presence of Triazabicyclodecene at a Molar Ratio of Carbamate to Catalyst of 18.5:1 (Comparative Example Using a Catalyst with an Excessively Low $pK_B$)

In an inertized multi-neck flask, 0.75 g (4.21 mmol) of phenanthrene and also 0.31 g (2.23 mmol) of 3,4,6,7,8,9-hexahydro-2H-pyrimido[1,2-a]pyrimidine (triazabicyclodecene, TBD, $pK_B$=−0.47) were dissolved in 30.02 g (176.37 mmol) of diphenyl ether. The reaction mixture was heated to 215° C. In an inertized Schlenk tube, 6.25 g (41.34 mmol) of methyl N-phenylcarbamate were heated to 150° C. Completely transferring the methyl N-phenylcarbamate into the reaction mixture resulted in a mixture having a temperature of 200° C. This temperature was held constant for 120 minutes. The gaseous reaction products formed were driven out at an argon inert gas flow of 10 l/h and collected in a cold trap. The progress of the reaction was monitored by means of continuous sampling from the reaction vessel and subsequent analysis by means of NMR spectroscopy.

The yield of phenyl isocyanate was 2% with a selectivity of 2%.

Example 12: Conversion of Methyl N-Phenylcarbamate into Phenyl Isocyanate by Cleavage at 200° C. in the Presence of Sodium Hydrogensulfate (Catalyst of Type (C)) at a Molar Ratio of Carbamate to Catalyst of 18.3:1

In an inertized multi-neck flask, 0.63 g (3.53 mmol) of phenanthrene and also 0.22 g (1.83 mmol) of sodium hydrogensulfate were dissolved in 30.64 g (180.16 mmol) of diphenyl ether. The reaction mixture was heated to 215° C. In an inertized Schlenk tube, 5.07 g (33.56 mmol) of methyl N-phenylcarbamate were heated to 150° C. Completely transferring the methyl N-phenylcarbamate into the reaction mixture resulted in a mixture having a temperature of 200° C. This temperature was held constant for 120 minutes. The gaseous reaction products formed were driven out at an argon inert gas flow of 10 l/h and collected in a cold trap. The progress of the reaction was monitored by means of continuous sampling from the reaction vessel and subsequent analysis by means of $^1$H NMR spectroscopy.

The yield of phenyl isocyanate was 42% with a selectivity of 90%.

Example 13: Conversion of Methyl N-Phenylcarbamate into Phenyl Isocyanate by Cleavage at 200° C. in the Presence of Sodium Sulfate at a Molar Ratio of Carbamate to Catalyst of 19.3:1 (Comparative Example to Example 12)

In an inertized multi-neck flask, 0.59 g (3.31 mmol) of phenanthrene and also 0.25 g (1.76 mmol) of sodium sulfate were dissolved in 30.17 g (177.25 mmol) of diphenyl ether. The reaction mixture was heated to 216° C. In an inertized Schlenk tube, 5.13 g (33.96 mmol) of methyl N-phenylcarbamate were heated to 150° C. Completely transferring the methyl N-phenylcarbamate into the reaction mixture resulted in a mixture having a temperature of 200° C. This temperature was held constant for 120 minutes. The gaseous reaction products formed were driven out at an argon inert gas flow of 10 l/h and collected in a cold trap. The progress of the reaction was monitored by means of continuous sampling from the reaction vessel and subsequent analysis by means of $^1$H NMR spectroscopy.

The yield of phenyl isocyanate was 17% with a selectivity of 92%.

Example 14: Conversion of Methyl N-Phenylcarbamate into Phenyl Isocyanate by Cleavage at 200° C. in the Presence of Sulfuric Acid at a Molar Ratio of Carbamate to Catalyst of 19.1:1 (Comparative Example to Example 12)

In an inertized multi-neck flask, 0.62 g (3.48 mmol) of phenanthrene and also 0.17 g (1.73 mmol) of sulfuric acid were dissolved in 30.44 g (178.83 mmol) of diphenyl ether. The reaction mixture was heated to 216° C. In an inertized Schlenk tube, 4.99 g (33.03 mmol) of methyl N-phenylcarbamate were heated to 150° C. Completely transferring the methyl N-phenylcarbamate into the reaction mixture resulted in a mixture having a temperature of 200° C. This temperature was held constant for 120 minutes. The gaseous reaction products formed were driven out at an argon inert gas flow of 10 l/h and collected in a cold trap. The progress of the reaction was monitored by means of continuous sampling from the reaction vessel and subsequent analysis by means of $^1$H NMR spectroscopy.

The yield of phenyl isocyanate was 17% with a selectivity of 89%.

Example 15: Conversion of 4-Methoxyphenyl N-Phenylcarbamate into Phenyl Isocyanate by Cleavage at 200° C. in the Presence of Sodium Hydrogensulfate (Catalyst of Type (C)) at a Molar Ratio of Carbamate to Catalyst of 15.9:1

In an inertized multi-neck flask, 0.62 g (3.48 mmol) of phenanthrene and also 0.25 g (2.08 mmol) of sodium hydrogensulfate were dissolved in 29.95 g (175.96 mmol) of diphenyl ether. The reaction mixture was heated to 215° C. In an inertized Schlenk tube, 8.05 g (33.09 mmol) of 4-methoxyphenyl N-phenylcarbamate were heated to 150° C. Completely transferring the 4-methoxyphenyl N-phenylcarbamate into the reaction mixture resulted in a mixture having a temperature of 200° C. This temperature was held constant for 120 minutes. The gaseous reaction products formed were driven out at an argon inert gas flow of 10 l/h and collected in a cold trap. The progress of the reaction was monitored by means of continuous sampling from the reaction vessel and subsequent analysis by means of HPLC chromatography.

The yield of phenyl isocyanate was 50% with a selectivity of 71%.

Example 16: Conversion of 4-Methoxyphenyl N-Phenylcarbamate into Phenyl Isocyanate by Thermal Cleavage at 200° C. in Diphenyl Ether (Comparative Example to Example 15)

In an inertized multi-neck flask, 0.61 g (3.42 mmol) of phenanthrene were dissolved in 30.10 g (176.84 mmol) of diphenyl ether. The reaction mixture was heated to 215° C. In an inertized Schlenk tube, 8.03 g (33.01 mmol) of 4-methoxyphenyl N-phenylcarbamate were heated to 150° C. Completely transferring the 4-methoxyphenyl N-phenylcarbamate into the reaction mixture resulted in a mixture having a temperature of 200° C. This temperature was held constant for 120 minutes. The gaseous reaction products formed were driven out at an argon inert gas flow of 10 l/h and collected in a cold trap. The progress of the reaction was monitored by means of continuous sampling from the reaction vessel and subsequent analysis by means of HPLC chromatography.

The yield of phenyl isocyanate was 27% with a selectivity of 84%.

Example 17: Conversion of 4-Tert-Butylphenyl N-Phenylcarbamate into Phenyl Isocyanate by Cleavage at 200° C. in the Presence of Sodium Hydrogensulfate (Catalyst of Type (C)) at a Molar Ratio of Carbamate to Catalyst of 15.3:1

In an inertized multi-neck flask, 0.64 g (3.59 mmol) of phenanthrene and also 0.26 g (2.17 mmol) of sodium hydrogensulfate were dissolved in 30.16 g (177.19 mmol) of diphenyl ether. The reaction mixture was heated to 215° C. In an inertized Schlenk tube, 8.94 g (33.19 mmol) of 4-tert-butylphenyl N-phenylcarbamate were heated to 150° C. Completely transferring the 4-tert-butylphenyl N-phenylcarbamate into the reaction mixture resulted in a mixture having a temperature of 200° C. This temperature was held constant for 120 minutes. The gaseous reaction products formed were driven out at an argon inert gas flow of 10 l/h and collected in a cold trap. The progress of the reaction was monitored by means of continuous sampling from the reaction vessel and subsequent analysis by means of HPLC chromatography.

The yield of phenyl isocyanate was 48% with a selectivity of 74%.

Example 18: Conversion of 4-Tert-Butylphenyl N-Phenylcarbamate into Phenyl Isocyanate by Thermal Cleavage at 200° C. in Diphenyl Ether (Comparative Example to Example 17)

In an inertized multi-neck flask, 0.60 g (3.37 mmol) of phenanthrene were dissolved in 31.26 g (183.67 mmol) of diphenyl ether. The reaction mixture was heated to 215° C. In an inertized Schlenk tube, 8.76 g (32.52 mmol) of 4-tert-butylphenyl N-phenylcarbamate were heated to 150° C. Completely transferring the 4-tert-butylphenyl N-phenylcarbamate into the reaction mixture resulted in a mixture having a temperature of 200° C. This temperature was held constant for 120 minutes. The gaseous reaction products formed were driven out at an argon inert gas flow of 10 l/h and collected in a cold trap. The progress of the reaction was monitored by means of continuous sampling from the reaction vessel and subsequent analysis by means of HPLC chromatography.

The yield of phenyl isocyanate was 23% with a selectivity of 87%.

The invention claimed is:
1. A process for producing an isocyanate in which a carbamate or thiolcarbamate is converted into the corresponding isocyanate in the presence of a catalyst with elimination of an alcohol or thioalcohol at a temperature of at least 150° C., wherein the catalyst used is-comprises a compound of the general formula (X)(Y)(Z—H), where:

(A)
X is $N(R^1)$,
Y is $C(R^2)$ or is a bridge formed of 2 carbon atoms which are part of a ring system comprising 5 or 7 carbon atoms with alternating double and single bonds, or is a bridge formed of 3, 5 or 7 carbon atoms with alternating single and double bonds, and
Z is O, S, $N(R^6)$ or $N^{(+)}(R^7)(R^8)$, and
wherein the catalyst has a $pK_B$ at 25° C. of ≥3.00; or (B)
X is O,
Y is $C(R^2)$ or is a bridge formed of 2 carbon atoms which are part of a ring system comprising 5 or 7 carbon atoms with alternating double and single bonds, or is a bridge formed of 3, 5 or 7 carbon atoms with alternating single and double bonds, and
Z is O; or (C)
X is O,
Y is $S(O)(R^3)$ or $P(OR^4)(OR^5)$, and Z is O;
where:
$R^1$ is:
an optionally substituted aromatic or araliphatic radical having 6 to 10 carbon atoms, or
an optionally substituted aliphatic radical having 1 to 6 carbon atoms, or
joined to $R^2$ or $R^8$ to form a ring consisting of a total of 5 to 8 atoms, wherein the ring can optionally comprise heteroatoms, especially nitrogen and/or sulfur;
$R^2$ is:
hydrogen, or
an optionally substituted, aromatic or araliphatic radical having 6 to 10 carbon atoms, or
an optionally substituted, aliphatic radical having 1 to 6 carbon atoms and optionally comprising ether units, or
joined to $R^1$ or $R^6$ or $R^7$ to form a ring consisting of a total of 5 to 8 atoms, wherein the ring can optionally comprise one or more heteroatoms;
$R^3$ is
an aromatic or araliphatic radical having 6 to 10 carbon atoms which is substituted by a sulfonic acid group or sulfonate group, or
an aliphatic radical having 1 to 6 carbon atoms which is substituted by an amine group, sulfonic acid group or sulfonate group, or
$O^{(-)}M^{(+)}$, where $M^{(+)}$ is an alkali metal cation, imidazolium cation, pyridinium cation, pyrrolidinium cation, phosphonium cation, sulfonium cation or $NH_4^+$, or is a mono-, di-, tri- or tetrasubstituted organic ammonium cation the organic substituents of which independently of one another are selected from the group consisting of methyl, ethyl, propyl, butyl, pentyl, hexyl, phenyl and cyclohexyl;
$R^4$ and $R^5$ independently of one another are:
optionally substituted aromatic or araliphatic radicals each having 6 to 10 carbon atoms, where $R^4$ and $R^5$ may be joined to form a ring consisting of 5 to 8 atoms, or
optionally substituted aliphatic radicals each having 1 to 6 carbon atoms, where $R^4$ and $R^5$ may be joined to form a ring consisting of 5 to 8 atoms;
$R^6$ is:
an optionally substituted aromatic or araliphatic radical having 6 to 10 carbon atoms or
an optionally substituted aliphatic radical having 1 to 6 carbon atoms or joined to R² to form a ring consisting of a total of 5 to 8 atoms, wherein the ring can optionally comprise one or more heteroatoms;

R⁷ is:
an optionally substituted aromatic or araliphatic radical having 6 to 10 carbon atoms, or
an optionally substituted aliphatic radical having 1 to 6 carbon atoms, or
joined to R² to form a ring consisting of a total of 5 to 8 atoms, wherein the ring can optionally comprise one or more heteroatoms;

R⁸ is:
an optionally substituted aromatic or araliphatic radical having 6 to 10 carbon atoms, or
an optionally substituted aliphatic radical having 1 to 6 carbon atoms, or
joined to R¹ to form a ring consisting of a total of 5 to 8 atoms.

2. The process as claimed in claim 1, in which the conversion of the starting carbamate or starting thiolcarbamate is conducted in solution in the presence of an organic solvent selected from aprotic polar solvents without isocyanate-reactive groups.

3. The process as claimed in claim 2, in which a concentration of the starting carbamate or starting thiolcarbamate in the solution is 5% by mass to 95% by mass, based on the total mass of the solution.

4. The process as claimed in claim 1, in which a molar ratio of starting carbamate or starting thiolcarbamate to catalyst of 1000:1 to 1:1 is used.

5. The process as claimed in claim 1, in which the conversion is conducted at a temperature in the range from 150° C. to 280° C. and at a pressure in the range from 0.001 $bar_{(abs.)}$ to 2.00 $bar_{(abs.)}$.

6. The process as claimed in claim 1, in which the isocyanate formed and/or the alcohol or thioalcohol formed is/are removed from the reaction mixture continuously or at intervals.

7. The process as claimed in claim 6, wherein the removal of the alcohol or thioalcohol is effected by passing through a stripping gas and/or by distillation, optionally assisted by application of a pressure which is reduced compared to ambient pressure.

8. The process as claimed in claim 6, wherein either (i) both the isocyanate formed and the alcohol or thioalcohol formed are removed together, followed by a separation of a gaseous mixture obtained containing the isocyanate and the alcohol or thioalcohol by means of fractional condensation, or (ii) first the alcohol or thioalcohol and then the isocyanate is removed.

9. The process as claimed in claim 8, in which, for the removal of the alcohol or thioalcohol and of the isocyanate, the reaction mixture is distilled continuously in two series-connected distillation columns.

10. The process as claimed in claim 1, in which:
the isocyanate to be produced is butylene 1,4-diisocyanate, pentane 1,5-diisocyanate, hexamethylene 1,6-diisocyanate or the dimers, trimers, pentamers, heptamers or nonamers thereof or mixtures of same, isophorone diisocyanate, 2,2,4- and/or 2,4,4-trimethylhexamethylene diisocyanate, the isomeric bis(4,4'-isocyanatocyclohexyl)methanes or mixtures thereof in any desired proportions, cyclohexylene 1,4-diisocyanate, phenyl isocyanate, phenylene 1,4-diisocyanate, tolylene 2,4- and/or 2,6-diisocyanate, naphthylene 1,5-diisocyanate, diphenylmethane 2,2'- and/or 2,4'- and/or 4,4'-diisocyanate and/or the higher homologs thereof, 1,3- and/or 1,4-bis(2-isocyanatoprop-2-yl)benzene, 1,3-bis(isocyanatomethyl)benzene, or an alkyl 2,6-diisocyanatohexanoate (lysine diisocyanate) having alkyl groups of 1 carbon atom to 6 carbon atoms, and
the carbamate or thiolcarbamate used is the methyl, ethyl, n-propyl, isopropyl, n-butyl, isobutyl, tert-butyl, cyclohexyl or phenyl carbamate or thiolcarbamate or substituted methyl, ethyl, n-propyl, isopropyl, n-butyl, isobutyl, tert-butyl, cyclohexyl or phenyl carbamate or thiolcarbamate which corresponds to the isocyanate to be produced.

11. The process as claimed in claim 1, in which no further catalyst is used besides the catalyst (X)(Y)(Z)H.

12. The process as claimed in claim 1, in which the catalyst (X)(Y)(Z—H) is selected from the group consisting of 2-hydroxy-2,4,6-cycloheptatrien-1-one (tropolone); 2-acetyl-1-tetralone; N,N'-diphenylformamidine; N-(2,6-dimethylphenyl)-5,6-dihydro-4H-1,3-thiazin-2-amine (xylazine); 2,3-dihydro-7-azaindole; protonated N-methyl-1,5,7-triazabicyclo[4.4.0]dec-5-ene; protonated 1,8-diazabicyclo[5.4.0]undec-7-ene; O-methyl-N,N'-diisopropylisourea; 2-mercaptopyridine; 1,3,4-thiadiazole-2,5-dithiol; mercaptobenzimidazole; the constitutional isomers of the benzenedisulfonic acid monoanion; the constitutional isomers of benzenedisulfonic acid; (R)-(−)-1,1'-binaphthyl-2,2'-hydrogenphosphate; dibenzyl hydrogenphosphate; naphthalene-2,6-disulfonic acid monoanion; alkali metal hydrogensulfate, 2-aminoethane-1-sulfonic acid (taurine) and mixtures thereof.

13. The process as claimed in claim 1, in which a catalyst of type (A) is used.

14. The process as claimed in claim 1, in which a catalyst of type (B) is used.

15. The process as claimed in claim 1, in which a catalyst of type (C) is used.

* * * * *